United States Patent [19]

Phillips

[11] Patent Number: 5,648,142
[45] Date of Patent: Jul. 15, 1997

[54] PERFORATED FILMS HAVING CHANNELS WITH CUTOUT PORTIONS CAPABLE OF SPONTANEOUS FLUID INVERSION

[75] Inventor: Bobby Mal Phillips, Jonesborough, Tenn.

[73] Assignee: Eastman Chemical Company, Kingsport, Tenn.

[21] Appl. No.: 545,450

[22] Filed: Oct. 19, 1995

[51] Int. Cl.$^6$ .................................. B32B 3/10; A61F 13/52
[52] U.S. Cl. .................... 428/132; 428/137; 428/131; 428/134; 428/195; 428/913; 604/383; 604/378
[58] Field of Search ........................ 428/132, 137, 428/131, 134, 195, 913; 604/383, 378

[56] References Cited

U.S. PATENT DOCUMENTS

| | | | |
|---|---|---|---|
| 3,929,135 | 12/1975 | Thompson | 128/287 |
| 4,535,020 | 8/1985 | Thomas et al. | 428/131 |
| 4,634,440 | 1/1987 | Widlund et al. | 604/383 |
| 4,637,819 | 1/1987 | Ouellette et al. | 604/369 |
| 4,735,843 | 4/1988 | Noda | 428/137 |
| 4,781,710 | 11/1988 | Megison et al. | 604/378 |
| 4,895,749 | 1/1990 | Rose | 428/132 |
| 5,078,710 | 1/1992 | Suda et al. | 604/383 |
| 5,268,213 | 12/1993 | Murakami et al. | 428/163 |
| 5,275,863 | 1/1994 | Hanson | 428/136 |
| 5,368,909 | 11/1994 | Langdon et al. | 428/137 |
| 5,383,870 | 1/1995 | Takai et al. | 604/378 |
| 5,387,209 | 2/1995 | Yamamoto et al. | 604/384 |

*Primary Examiner*—William Watkins
*Attorney, Agent, or Firm*—Cheryl J. Tubach; Harry J. Gwinnell

[57] ABSTRACT

A polymeric film for use in absorbent structures comprises a planar surface having a frontside, a backside and a plurality of apertures. Walls extend from the perimeter of the apertures and outwardly from the backside. The walls and the backside form a capillary system on the backside. The walls form channels which connect the frontside of the film to the capillary system on the backside. The walls have at least one cut out portion extending the length of the walls. A fluid contacting the frontside of the film will spontaneously invert to the capillary system on the backside of the film through the cut out portions of the walls.

12 Claims, 2 Drawing Sheets

5,648,142

PERFORATED FILMS HAVING CHANNELS WITH CUTOUT PORTIONS CAPABLE OF SPONTANEOUS FLUID INVERSION

TECHNICAL FIELD

This invention relates generally to absorbent products, and more particularly to absorbent products having top sheets made from apertured films which freely transport and disperse liquids to the backside of the top sheet.

BACKGROUND OF THE INVENTION

Absorbent devices for receiving and retaining bodily fluid are well known. They typically are designed with a top sheet made of a polymeric film having apertures or perforations therein, an absorbent core, and a bottom sheet or outer layer made of a liquid impervious material for retaining fluids. The top sheet is in contact with the body and the first to receive the bodily fluids which pass through the apertures into the absorbent core. The bottom sheet prevents the fluids in the core from leaking out of the absorbent devices.

U.S. Pat. No. 3,929,135 to Thompson discloses an absorbent product with a top sheet having tapered capillaries. Each capillary has a base in the plane of the sheet and an apex remote from the plane of the sheet. The apexes are in intimate contact with an absorbent core. U.S. Pat. No. 4,634,440 to Windlund et al. discloses a top sheet having apertures with straight ducts which are of uniform width along their entire length. The ends of the ducts that project away from the top sheet have fibers extending therein which connect the ducts to an absorbent core. The absorbent cores are typically made of a material having high capillary suction, such as fluff pulp. In order for these designs to transfer fluid effectively, the material with higher capillary suction must be in contact with the apexes of the capillaries or the ends of the ducts. This is typically accomplished by adhering the absorbent core to the backside of the top sheet. However, quite often undesirable separation of the sheet and absorbent core occurs which causes the product not to perform properly. The fluid travels to the bottoms of the capillaries and stops, excess fluid then builds up on the frontside of the top sheet and leakage occurs due to fluid run off, as shown in FIG. 1.

Thus, there exists a need in the art for an apertured or perforated sheet which has the unique ability to spontaneously invert fluids from the frontside of the sheet through to the backside of the sheet without the need of any absorbent core material being in contact with the backside of the sheet.

SUMMARY OF THE INVENTION

A polymeric film for use in absorbent structures comprises a planar surface having a frontside, a backside coated with a hydrophilic material and a plurality of apertures. Walls extend from the perimeter of the apertures and outwardly from the backside. The walls and the backside form a capillary system on the backside. The walls form channels which connect the frontside of the film to the capillary system on the backside. The walls have at least one cut out portion extending the length of the walls. A fluid contacting the frontside of the film will spontaneously invert to the capillary system on the backside of the film through the cut out portions of the walls.

DETAILED DESCRIPTION OF THE DRAWINGS

Figure 2A:
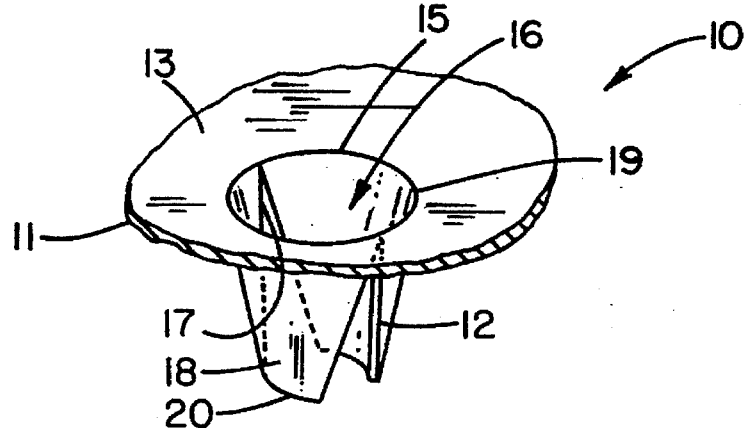
FIG. 2a is a top perspective view of a conically shaped channel extending from an aperture in a film of a preferred embodiment of the invention.
Figure 2B:
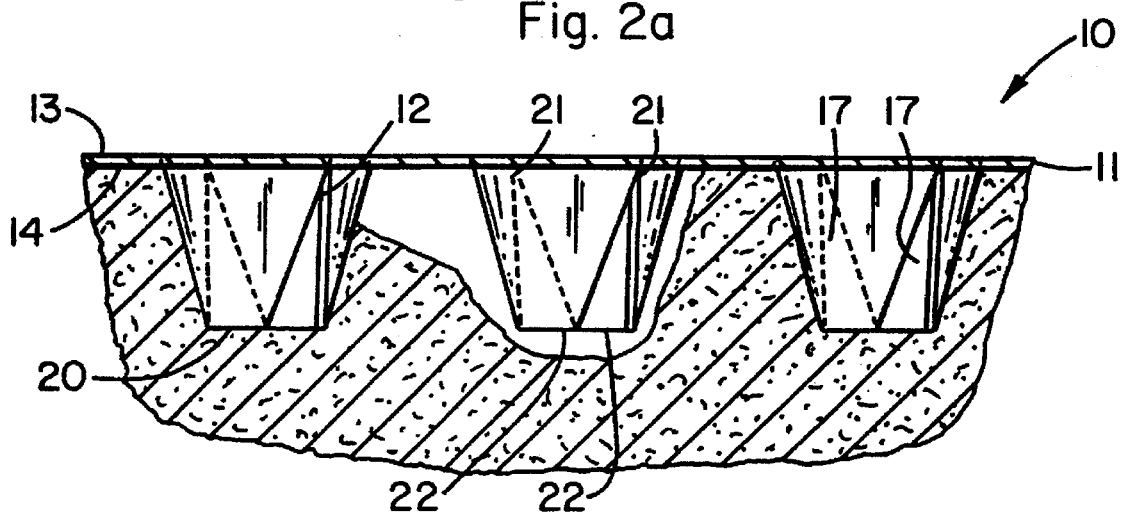
FIG. 2b is a side view of several conically shaped channels of FIG. 2a in an absorbent structure.

Referring now in more detail to the drawings, in which like numerals indicate like parts throughout the several views, a portion of a film 10 made of a film-forming polymer is shown in FIG. 2a and 2b. The thickness of the film 10 is from about 0.001 to about 0.002 inches. The polymer may be polyethylene or polypropylene.

The film 10 has a planar surface 11 and a plurality of walls 12. The planar surface 11 has a frontside 13, a backside 14, and apertures 15. The walls 12 extend outwardly from the backside 14 along the perimeter of the apertures 15. The walls 12 and the backside 14 form a capillary system on the backside which provides for fluid transport. The walls 12 form channels 16 which connect the frontside 13 to the backside 14. The walls 12 have cut out portions 17 that extend the length of the walls.

The apertures 15 are substantially circular, thus the walls 12 of the channels 16 which extend outwardly from the backside 14 form cones 18. The cones 18 are positioned such that their bases 19 are at the planar surface 11. The perimeters of the bases 19 are also the perimeters of the apertures 15. The diameters of the apertures/bases are from about 0.006 to about 0.25 inches, preferably 0.03 to 0.06 inches. The apexes 20 of the cones 18, which are distal to the planar surface 11, are substantially open such that the fluid entering the cones from the frontside 13 of the planar surface flow through the channels 16 to the backside 14. The diameters of the apexes 20 are from about 0.004 to about 0.10 inches, preferably 0.005 to 0.02 inches. The angles between the backside 14 and the walls 12, which causes the walls 12 to taper, are preferably greater than 90° and less than 135°. The number of cones 18 per square inch, which also refers to the number of channels and apertures, is from about 30 to 1500, preferably 400 to 900.

The cut out portions 17 on the walls 12 of the channels 16 are preferably triangular. The vertices 21 of the cut out portions 17 are adjacent to the planar surface 11 and the bases 22 are distal thereto. Such orientation of the cut out portions 17 is opposite to that of the cones 18. The vertices 21 of the cut out portions preferably adjoin the planar surface 11 at the perimeters of the apertures 11 to maximize fluid flow. However, the vertices 21 may be slightly below the planar surface 11.

Figure 3:
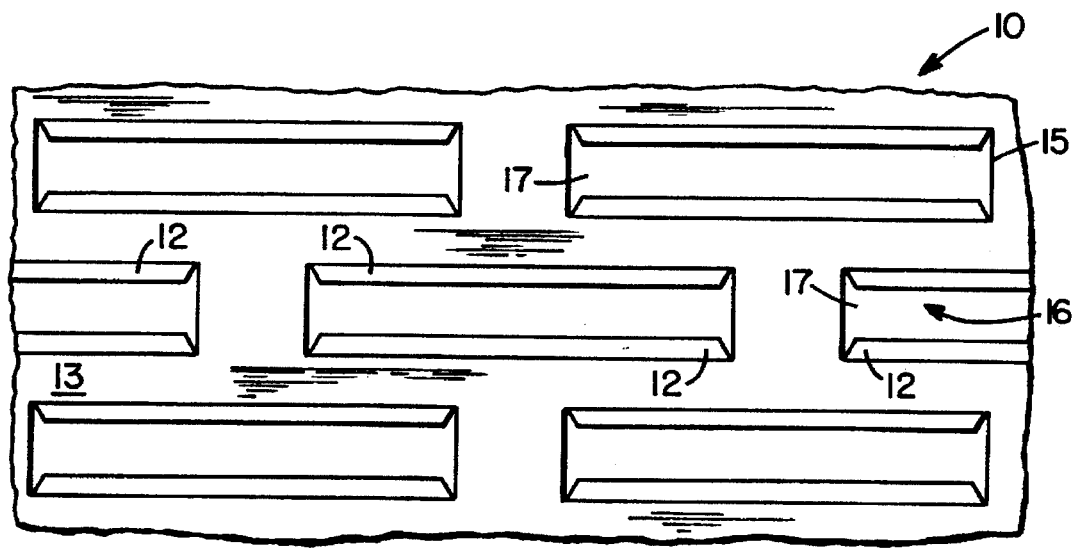
FIG. 3 is a top view of a portion of an absorbent structure having rectangular shaped channels of another preferred embodiment of the invention.

Another preferred embodiment is shown in FIG. 3. The apertures 15, and therefore the channels 16, are rectangular. The walls 12 of the channels 16 taper inwardly forming a rectangular trough-like area. The angles between the backside 14 of the film 10 and the walls 12 are greater than 90° and less than 135°. The cut out portions 17 are the opposing shorter walls 12 of the rectangular channels 16 rather than opposing triangular portions of the cones 18, as discussed above. The length/width ratios of the rectangular apertures may be from 1/1 to 10/1.

Figure 4:
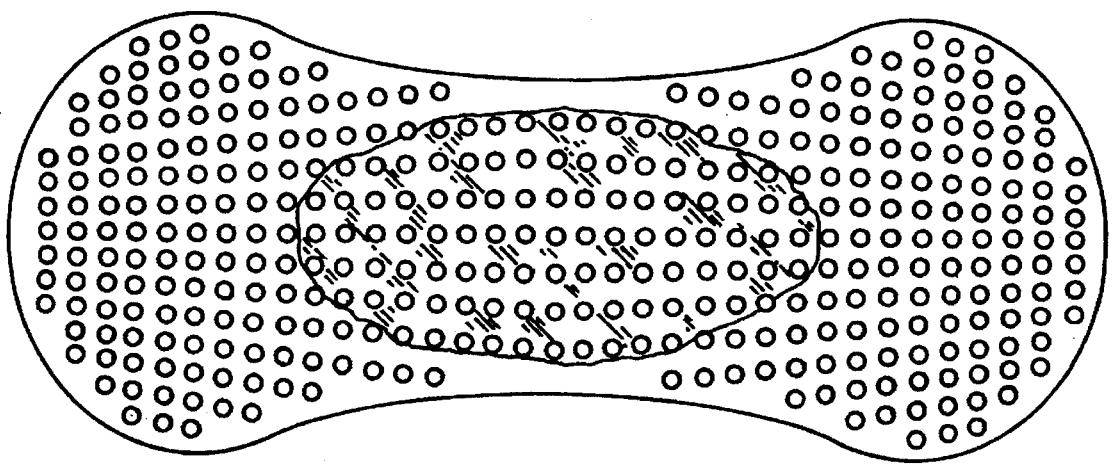
FIG. 4 is a top view of a preferred arrangement of an absorbent structure having the apertures of FIG. 2.

The films of the present invention spontaneously invert fluids from the frontside 13 to the backside 14 of the film 10 through the channels 16 and cut out portions 17. The spontaneous inversion results from the capillary action created by the cut out portions 17 and the capillary system on backside 14 of the film 10. The inverted fluid has a preferred directional movement in the capillary system on the backside of the film. Preferably, the preferred directional movement of the fluid is at least 1.5 times the movement in the direction perpendicular thereof. This preferred directional movement of the fluid may be accomplished by positioning the cones 18, i.e. channels 16, in a converging pattern from a middle section to opposing outer sections of the capillary system, as shown in FIG. 4. Such pattern provides for a definite shape of the capillary system on the backside of the film and moves fluid preferably through the length of the capillary system in an elliptical pattern.

Figure 1:
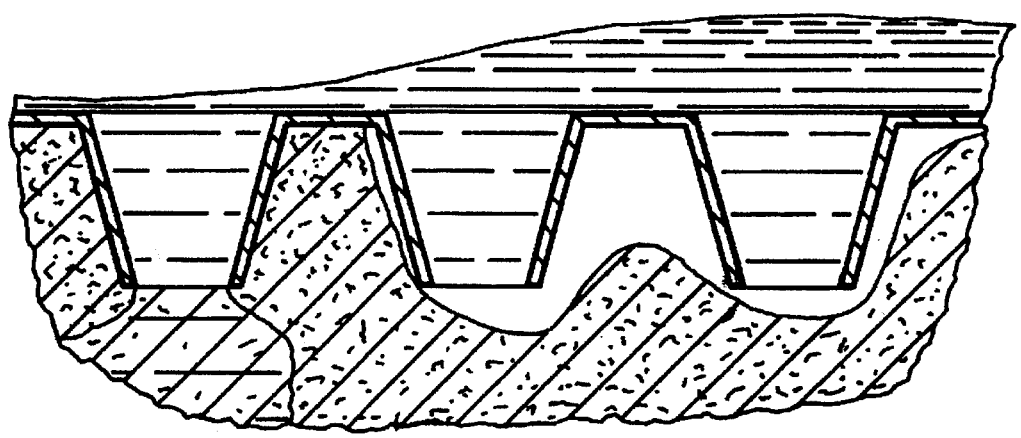
FIG. 1 is a cross-sectional view of a portion of a prior art absorbent structure showing fluid build-up thereon due to the separation of the absorbent core from the apertured top sheet.

Other film variations, such as the shapes of the channels, the number of channels having cut out portions in their walls and the number of cut out portions per channel, may be used to provide for spontaneous inversion of fluid. The appropriate number of channels having cut out portions must be large enough such that the fluid spontaneously inverts to the capillary system on the backside of the film. The number of cut out portions per channel may also vary as long as the structure of the channel itself is not destroyed. These variations depend on the amount of fluid flow and desired speed of fluid inversion needed for each application. The spontaneous fluid inversion may be enhanced by applying a light coating of a hydrophilic material, such as polyethylene glycol, to the backside 14 of the film 10. For the films of the present invention, there is no need for an absorbent material like fluff pulp to be in contact with the apexes 20 of the cones 18 as in FIG. 2. To the contrary, the prior art films of FIG. 1 require at least some portion of an absorbent material to be in contact with the backside of the film and or the apexes of the cones. Otherwise, fluid builds up on the frontside causing problems such as side leakage.

The films of the present invention are useful as top sheets in absorbent structures such as diapers, catamenials, adult incontinent products, training pants. The top sheets are the surface upon which the fluid first makes contact. Controlling the flow of the inverted fluid edge on the backside of the top sheet is highly desired in order to make absorbent structures more effective in spontaneous fluid inversion. The controlled flow of such fluid is accomplished by providing a pattern in the apertures on the frontside of the top sheet and, thus, also in the cones on the backside, as discussed above. The pattern of FIG. 4 creates fluid movement in an essentially elliptical flow pattern with the major axis of the ellipse being coincident with the major axis of a catamenial pad. This pattern is desirable because it causes the fluid to move to the ends of the pad and not to the sides, thus substantially limiting side leakage of the pad. Note that FIG. 4 is not drawn to scale and the apertures are actually much smaller on the pad than shown.

Absorbent structures using these films as top sheets have the ability to significantly reduce leakage during use. These films are especially useful when used in conjunction with spontaneously wettable fibers as a core component in an absorbent product. With spontaneously wettable fibers the spontaneous fluid inversion into the capillary system on the backside of the top sheet allows many more spontaneously wettable fibers to operate in draining the fluid into the core. Preferably, the spontaneously wettable fibers are those as disclosed in EP 0 536 308.

The present invention provides for improved apertured top sheets for absorbent structures. The polymeric film with its cut out portions in the walls of the cones extending from the apertures and the coating of hydrophilic material on the backside forms a top sheet that will spontaneously invert fluid from its contact side to the capillary system on its backside. The specific pattern of the apertures and the cut out portions of the cones direct the fluid flow on the backside through the capillary system such that side leakage is significantly eliminated thereby improving performance of absorbent structures.

The invention has been described in detail with particular reference to preferred embodiments thereof, but it will be understood that variations and modifications can be effected within the spirit and scope of the invention.

What is claimed is:

1. A polymeric film made for use in absorbent structures comprising a planar surface and a plurality of walls;
   said planar surface having a frontside, a backside coated with a hydrophilic material and a plurality of apertures;
   said plurality of walls extending from the perimeter of said apertures and outwardly from said backside;
   said walls and said backside forming a capillary system on said backside;
   said walls forming channels connecting said frontside to said capillary system on said backside; and
   a plurality of said walls having at least one cut out portion,
   whereby a fluid contacting the frontside of the film spontaneously inverts to the capillary system on the backside of the film through the cut out portions of the walls.

2. The film of claim 1 wherein the inverted fluid has a preferred directional movement in said capillary system on said backside of said film.

3. The film of claim 2 wherein said preferred directional movement of the fluid is at least 1.5 times the movement in the direction perpendicular to said preferred directional movement.

4. The film of claim 2 wherein said channels are positioned in a converging pattern from a middle section to opposing outer sections of said capillary system whereby the converging pattern causes the preferred directional movement of the fluid to be in an elliptical pattern through the length of the capillary system.

5. The film of claim 1 wherein each said channel has at least one said cut out portion in said wall.

6. The film of claim 1 wherein said cut out portions extend along the length of said walls.

7. The film of claim 1 wherein said apertures are substantially circular, said walls of said channels form cones each having a base at said planar surface and an open apex distal thereto, and the angle between said backside and said walls is greater than 90° and less than 135°.

8. The film of claim 7 wherein said cut out portions are triangular with vertices adjacent to said planar surface and bases distal thereto.

9. The film of claim 8 wherein said vertices of said cut out portions adjoin said planar surface at the perimeters of said apertures.

10. The film of claim 8 wherein said vertices of said cut out portions are slightly below said planar surface.

11. The film of claim 1 wherein said apertures and said channels are rectangular, said walls of said channels taper inwardly and the angle between said backside and said walls is greater than 90° and less than 135°.

12. The film of claim 11 wherein said cut out portions are on opposing walls of said channels.

* * * * *